US009364197B2

(12) United States Patent
Rao et al.

(10) Patent No.: US 9,364,197 B2
(45) Date of Patent: Jun. 14, 2016

(54) DEVICE AND METHOD FOR IMPROVING IDENTIFICATION ACCURACY OF FETAL HEART RATE DECELERATION (71) Applicant: EDAN INSTRUMENTS, INC., Nanshan Shenzhen (CN)

(72) Inventors: Jian Rao, Shenzhen (CN); Wusun Chen, Shenzhen (CN); Yonghua Zeng, Shenzhen (CN); Dewei Chen, Shenzhen (CN)

(73) Assignee: EDAN INSTRUMENTS, INC, Shenzhen (CN)

( * ) Notice: Subject to any disclaimer, the term of this patent is extended or adjusted under 35 U.S.C. 154(b) by 71 days.

(21) Appl. No.: 14/349,326

(22) PCT Filed: Sep. 26, 2012

(86) PCT No.: PCT/CN2012/082019
§ 371 (c)(1),
(2) Date: Apr. 2, 2014

(87) PCT Pub. No.: WO2013/053290
PCT Pub. Date: Apr. 18, 2013

(65) Prior Publication Data
US 2014/0243674 A1  Aug. 28, 2014

(30) Foreign Application Priority Data

Oct. 13, 2011  (CN) .......................... 2011 1 0309679

(51) Int. Cl.
A61B 5/04        (2006.01)
A61B 8/08        (2006.01)
A61B 5/0444      (2006.01)
A61B 5/024       (2006.01)
A61B 8/02        (2006.01)
(52) U.S. Cl.
CPC .......... *A61B 8/5207* (2013.01); *A61B 5/02411* (2013.01); *A61B 5/0444* (2013.01); *A61B 8/02* (2013.01); *A61B 8/0866* (2013.01); *A61B 8/488* (2013.01); *A61B 8/5223* (2013.01)

(58) Field of Classification Search
CPC . A61B 5/0444; A61B 5/4362; A61B 5/02411
USPC ........................................................ 600/511
See application file for complete search history.

(56) References Cited

U.S. PATENT DOCUMENTS

2004/0133115 A1   7/2004  Hamilton
2006/0229518 A1  10/2006  Ofek
2009/0054797 A1   2/2009  Miller

FOREIGN PATENT DOCUMENTS

CN         1323012 A     11/2001
(Continued)

OTHER PUBLICATIONS

International Search Report dated Nov. 14, 2012.

*Primary Examiner* — Christopher D Koharski
*Assistant Examiner* — Philip C Edwards
(74) *Attorney, Agent, or Firm* — Symbus Law Group, LLC; Clifford D. Hyra (57) ABSTRACT

A device and method for improving the identification accuracy of fetal heart rate deceleration. The method includes: collecting fetal heart rate data (101); performing baseline identification on the collected fetal heart rate data (102); preprocessing the collected fetal heart rate data (103); performing deceleration identification on the preprocessed fetal heart rate data according to preset deceleration judgment standards and a fetal heart rate data baseline to obtain a decelerated data segment (104); and calculating a deceleration attribute value of each decelerated data segment (105), and outputting the decelerated data segment and calculation result (106). The present invention can effectively eliminate the baseline variation part by employing methods such as the dynamic threshold area method, continuous wave peak detection and composite deceleration detection and so on, and accurately identify each deceleration and the type thereof, avoiding the defects of the existing method, which easily causes large deceleration identification errors but cannot identify continuous deceleration or eliminate baseline variation and cannot identify composite deceleration and so on. The solution in the present invention is not only suitable for the situation where deceleration occurs independently and is typical deceleration but also is suitable for the situation where continuous deceleration and composite deceleration occur.

15 Claims, 5 Drawing Sheets

(56) References Cited

FOREIGN PATENT DOCUMENTS

| | | |
|---|---|---|
| CN | 1942135 A | 4/2007 |
| CN | 102048534 A | 5/2011 |
| CN | 102048558 A | 5/2011 |
| CN | 102090883 A | 6/2011 |
| CN | 102210586 A | 10/2011 |
| GB | 2471667 A | 1/2011 |

FIG. 9

DEVICE AND METHOD FOR IMPROVING IDENTIFICATION ACCURACY OF FETAL HEART RATE DECELERATION

This application claims the benefit of Chinese patent application No. 201110309679.9, filed Oct. 13, 2011, which is hereby incorporated by reference in its entirety.

FIELD OF THE INVENTION

The invention relates to the field of biomedical signal processing and specifically to a device for improving the identification accuracy of fetal heart rate deceleration and a realizing method thereof.

BACKGROUND OF THE INVENTION

Fetal heart rate deceleration is the most simple and effective method which provides reference and analysis for judging whether a fetus is safe during the delivery period. During the whole delivery course, about 50% to 70% of delivery cases have fetal heart rate deceleration. Their representative cases are early deceleration, late deceleration and variable deceleration. Early deceleration is generally caused because the fetal head is compressed, which has little relation with fetal hypoxia. However, if the early deceleration occurs during the early phase of the delivery course, the umbilical cord is compressed and the fetus may have hypoxia. Late deceleration is generally caused because the lack of oxygen causes the vagus nerve to have hyperactivity and/or myocardium is inhibited, which is generally regarded as reference. It mainly occurs during the uterus-placental blood flow reduction and fetal hypoxia caused by placental dysfunction. Variable deceleration is mainly caused because the umbilical cord is compressed. When severe variable deceleration or atypical variable deceleration occurs, they prompt that the fetus is distressed.

Currently, there are no uniform quantitative criteria for clinically judging fetal heart rate deceleration and the type thereof. Therefore, the method for clinically and automatically identifying the fetal heart rate deceleration data are calculated mainly according to the deceleration standard set by the duration, decrease amplitude and other experiential parameters. That is, a fetal monitoring module firstly collects the fetal heart rate, identifies the fetal heart rate baseline, and then calculates the number of decelerations and the duration, amplitude, types and so on under the baseline, according to the standard set by clinical deceleration experiential parameters. However, such method for identifying deceleration with the experiential parameters in the clinical application has the following disadvantages: firstly, as there are various deceleration types in the clinical environment; the experiential parameters are not necessarily accurate and may not cover all cases, thus facilitating the deceleration identification data to have large errors; Secondly, the method may not identify continuous deceleration and not eliminate the baseline variation part, thus resulting in the number of identified deceleration data being lower than the actual number and resulting in counting the baseline variation part into the deceleration; thirdly, there may be the mixing of many deceleration types during the delivery; The method may only identify one type of one deceleration datum and may not identify the composite deceleration data.

The experiential parameters may not meet the requirements of automatic deceleration identification. The objective of the invention is to overcome the following disadvantages: the deceleration errors identified according to the fetal heart rate deceleration automatic identification method in the prior art are large; continuous deceleration may not be identified; the baseline variation may not be eliminated; and composite deceleration may not be identified. The invention, with a dynamic threshold area algorithm, a continuous peak inspection algorithm and a composite deceleration inspection algorithm, may effectively eliminate the baseline variation part and accurately identify each deceleration and the type thereof.

SUMMARY OF THE INVENTION

In order to overcome the abovementioned disadvantages, the objective of the invention is to propose a device and method for improving the identification accuracy of fetal heart rate data deceleration.

The objective is realized through the following technical proposals:

the device comprises a fetal heart rate data collection module, a fetal heart rate data baseline identification module, a fetal heart rate data preprocessing module, a fetal heart rate data deceleration identification module and an output module, wherein the fetal heart rate data collection module is used for collecting the fetal heart data of preset duration to obtain a fetal heart rate data sequence H(n);

the fetal heart rate data baseline identification module is connected with the fetal heart rate data collection module to be used for receiving the fetal heart rate data sequence H(n) transmitted by the fetal heart rate data collection module and identifying a fetal heart rate baseline sequence B(n);

the fetal heart rate data preprocessing module is connected with the fetal heart rate data collection module to be used for receiving the fetal heart rate data sequence H(n) transmitted by the fetal heart rate data collection module and preprocessing the sequence H(n) to obtain a fetal heart rate data sequence V(n);

the fetal heart rate data deceleration identification module is connected with the fetal heart rate data baseline identification module and the fetal heart rate data preprocessing module to be used for receiving the fetal heart rate baseline sequence B(n) transmitted by the fetal heart rate data baseline identification module and the preprocessed sequence V(n) transmitted by the fetal heart rate data preprocessing module; and carrying out deceleration identification for the preprocessed fetal heart rate data sequence V(n) to obtain a decelerated data segment, according to the preset deceleration judgment standards and the fetal heart rate data baseline sequence B(n), and The output module is connected with the fetal heart rate data deceleration identification module to be used for receiving the decelerated data segment transmitted by the fetal heart rate data deceleration identification module and output it.

As a further technical proposal of the invention, the device for improving the identification accuracy of the fetal heart rate deceleration also comprises a fetal heart rate signal collection and processing transformation module, a fetal heart rate data deceleration validation module, a fetal heart rate data deceleration judgment standard setting module, a fetal heart rate data deceleration type judgment module, a collection duration setting and judgment module and a fetal heart rate data deceleration attribute calculation module, wherein the fetal heart rate signal collection and processing transformation module is connected with the fetal heart rate data collection module to be used for collecting a fetal heart signal, transforming the signal into the fetal heart rate data and transmitting the fetal heart rate data to the fetal heart rate data collection module;

the fetal heart rate deceleration validation module is connected with the fetal heart rate data deceleration identification module and the fetal heart rate data deceleration attribute calculation module to be used for receiving the decelerated data segment transmitted by the fetal heart rate data deceleration identification module; according to the loss condition of each decelerated signal, the fetal heart rate data deceleration validation module validates whether each decelerated sequence segment is real deceleration, and transmits the validation result to the fetal heart rate data deceleration attribute calculation module;

the fetal heart rate data judgment standard setting module is connected with the fetal heart rate deceleration identification module to be used for setting the fetal heart rate data deceleration judgment standard in advance and transmitting the judgment standard to the fetal heart rate data deceleration identification module;

the fetal heart rate data deceleration type judgment module is connected with the fetal heart rate data deceleration attribute calculation module to be used for judging the deceleration type under the conditions of collecting uterine contraction data and transmitting the judgment result to the fetal heart rate data deceleration calculation module;

the collection duration setting and judgment module is connected with the fetal heart rate data collection module to be used for setting the fetal heart rate collection duration and judging whether the collection data time exceeds the set duration; If the data collection time exceeds the set duration, the collection duration setting and judgment module transmits a timeout signal to the fetal heart rate data collection module;

the fetal heart rate data deceleration attribute calculation module is connected with the fetal heart rate data deceleration identification module and the output module to be used for receiving the deceleration data segment transmitted by the fetal heart rate data deceleration identification module, calculating the duration, amplitude and other deceleration attribute values of the each deceleration data segment and transmitting the calculated values to the output module.

As a further technical proposal of the invention, the fetal heart rate data preprocessing module further comprises:

an incorrect data processing unit used for processing the incorrect data of the fetal heart rate data sequence H(n) and obtaining the effective fetal heart rate data sequence V(n);

an interpolation processing unit used for fitting an invalid data part in the effective fetal heart rate data sequence V(n) with a linear interpolation method to obtain the fetal heart rate data sequence C(n).

As a further technical proposal of the invention, the fetal heart rate data deceleration identification module also comprises:

a standard comparison unit used for judging whether there is a sequence segment meeting a preset deceleration judgment standard in the fetal heart rate data sequence C(n);

a deceleration and variation unit used for inspecting and distinguishing deceleration and baseline variation sequence segments in the sequence C(n) meeting the standard, according to the fetal heart data sequence C(n) meeting the judgment standard and the corresponding baseline sequence B(n) thereof; and a deceleration number analysis unit used for analyzing the continuous deceleration number of a deceleration sequence in the sequence C(n) meeting the standard.

As a further technical proposal of the invention, the output module also comprises:

a display unit used for displaying an identified deceleration data segment and an attribute value thereof;

a printing unit used for printing and outputting the identified deceleration data segment and the attribute value thereof;

a storage unit used for storing the identified deceleration data segment and the attribute value thereof;

an identification unit used for identifying the identified deceleration data segment and the attribute value thereof.

A method for improving the identification accuracy of a fetal heart rate data deceleration, wherein, the method comprises:

Step 1, collecting the fetal heart rate data within a preset duration to obtain a fetal heart rate data sequence H(n);

Step 2, carrying out baseline identification for the fetal heart rate data sequence H(n) to obtain a fetal heart rate baseline data sequence B(n);

Step 3, preprocessing the fetal heart rate data sequence H(n) to obtain a preprocessed fetal heart rate data sequence C(n);

Step 4, carrying out deceleration identification for the preprocessed fetal heart rate sequence C(n) to obtain a decelerated data segment, according to the preset deceleration judgment standards and the fetal heart rate data baseline sequence B(n); and Step 5, outputting each the deceleration data segment and the calculation results of the deceleration attribute value thereof.

As a further technical proposal in the invention, before Step 1, the method further comprises: collecting and processing a fetal heart signal, transforming it and obtaining the fetal heart rate data.

As a further technical proposal of the invention, the method also comprises:

Step 31, processing the incorrect data of the fetal heart rate data sequence H(n) to obtain a sequence V(n);

Step 32, processing the interpolation of the sequence V(n) to obtain the preprocessed fetal heart rate data sequence C(n);

As a further technical proposal of the invention, Step 4 also comprises:

Step 41, the sequences C(n) and B(n) are input into the preset deceleration judgment standard, thus obtaining the set $$\{\{C_i\}_{S_i}^{E_i}\}_1^N$$

of each sequence segment meeting the deceleration standard in the sequence C(n) and the corresponding baseline sequence segment set $$\{\{B_i\}_{S_i}^{E_i}\}_1^N$$

thereof; if there is no sequence segment meeting the deceleration judgment standard, the user shall go back to Step 1 and collect the fetal heart rate data again;

Step 42, $$\{C_i\}_{S_i}^{E_i} \text{ and } \{B_i\}_{S_i}^{E_i}$$

are differenced to obtain sequence segment $$\{D_i\}_{S_i}^{E_i};$$

the continuous sequence segment, which is not more than threshold $R_0$, is sought in the sequence segment $\{D_i\}_{S_i}^{E_i}$; if there is no sequence segment meeting the condition in $$\{D_i\}_{S_i}^{E_i},$$

the sequence segment $$\{C_i\}_{S_i}^{E_i},$$

is judged to be a deceleration sequence segment; if there is a sequence segment meeting the condition in $$\{C_i\}_{S_i}^{E_i},$$

the sequence segment at the corresponding place and in the $$\{C_i\}_{S_i}^{E_i},$$

meeting the condition, is judged as the baseline variation part which is recorded as $$\left\{\{C'_j\}_{S'_j}^{E'_j}\right\}_1^M;$$

The baseline variation part divides $$\{C_i\}_{S_i}^{E_i}$$

into a plurality of segments, wherein $$\left\{\{\overline{C'_k}\}_{S'_k}^{E'_k}\right\}_1^{N_2}$$

judges whether $$\{\overline{C'_k}\}_{S'_k}^{E'_k}$$

meets the deceleration standard. If it meets the deceleration standard, the $$\{C'_k\}_{S'_k}^{E'_k}$$

is recorded as the deceleration sequence segment, otherwise, it is the baseline variation sequence segment, wherein $R_0$ is the parameter set in advance.

Step 43, the continuous sequence segment, which deviates from its corresponding baseline and of which the value exceeds threshold R1, is sought in the deceleration segment $$\{\overline{C'_k}\}_{S'_k}^{E'_k};$$

if there is no sequence segment meeting such condition, the $$\{\overline{C'_k}\}_{S'_k}^{E'_k}$$

is one deceleration; if there is a sequence segment meeting such condition, recording as $$\left\{\{\overline{C''_k}\}_{S''_k}^{E''_k}\right\}_1^{M_2};$$

and it is then analyzed whether each segment $$\{\overline{C''_k}\}_{S''_k}^{E''_k}$$

separately meets the deceleration standard; if the segment $$\{\overline{C''_k}\}_{S''_k}^{E''_k}$$

may meets the deceleration standard, the $$\{\overline{C''_k}\}_{S''_k}^{E''_k}$$

separately becomes the deceleration; otherwise, the $$\{\overline{C''_k}\}_{S''_k}^{E''_k}$$

is incorporated into the segment $$\{\overline{C''_k}\}_{S''_k}^{E''_k}.$$

Its adjacent segments are facilitated to be continuous and analyzed whether they meet the deceleration standard; if the deceleration standard is met, the continuous data segment becomes one deceleration; the subsequent segment data are analyzed according to the deceleration standard continuously again; otherwise, the baseline incorporates the segment until all of the segments are incorporated, wherein R1 is a preset parameter.

As the further technical proposal of the invention, after Step 4, the method also comprises: judging the signal loss situation of each deceleration data segment and validating whether each deceleration sequence segment is in real deceleration, according to the deceleration data segment.

As the further technical proposal of the invention, after Step 4, the method also comprises: judging the signal loss situation of each deceleration data segment according to the deceleration data segment; validating whether each deceleration sequence segment is in real deceleration further comprises:

a. comparing the sequences V(n) and C(n) and marking the interpolation place to obtain a marked sequence M(n);

b. as to each deceleration data segment, adjusting the places of original and destination points according to the sequence M(n) and facilitating the original and destination points not to be the interpolation points and to be closest to the interpolation point; and c. calculating the adjusted signal loss degree L; if the L exceeds threshold $\overline{L}$, the qualification of the deceleration is cancelled; otherwise, the qualification of the deceleration is retained, wherein $\overline{L}$ is a parameter set in advance.

As a further technical proposal of the invention, before Step 5, the method further comprises: calculating the deceleration attribute value of each deceleration data segment.

As a further technical proposal of the invention, before Step 5, calculating the deceleration attribute value of each deceleration data segment further comprises:

Step 51, calculating the duration $D_S$ according to the original point $D_E$ and the destination point $D_T$ of each deceleration, calculating the maximum amplitude $D_A$ deviating from the baseline in the deceleration and recording the place $D_P$ of the point (peak point);

Step 52, it is judged whether the uterine contraction data are collected at the same time; if the uterine contraction data are not collected, the type of the deceleration is not judged; if the uterine contraction data are collected, it is judged whether the deceleration data segment is early deceleration and/or late deceleration and/or variable deceleration and/or prolonged deceleration, according to the preset deceleration type judging conditions.

As a further technical proposal of the invention, Step 6 further comprises: displaying and/or printing and/or storing and/or identifying the deceleration data segment and the calculation results of the attribute values.

As a further technical proposal of the invention, the preset deceleration judgment standard in Step 4 also comprises:

Firstly: The fetal heart rate curves of the segment shall all be under the fetal heart rate baseline;

Secondly, the duration T under the fetal heart rate baseline shall be more than the threshold $T_0$; and Thirdly, the maximum amplitude A deviating the baseline shall be more than the threshold $A_0$.

Fourthly, the fetal heart rate curve of the segment and the corresponding baseline segment thereof are set as $$\{C_i\}_{S_i}^{E_i} \text{ and } \{B_i\}_{S_i}^{E_i},$$

respectively;

$$\{B_i\}_{S_i}^{E_i} \text{ and } \{C_i\}_{S_i}^{E_i}$$

are differenced to obtain the sequence segment $$\{D_i\}_{S_i}^{E_i}; \{D_i\}_{S_i}^{E_i}$$

is calculated with the compound trapezoid formula with step h to obtain the area S; and S shall be greater than or equal to the minimum value of the dynamic threshold $\beta$ and the static threshold $\alpha \times A \times T$;

If all of the above conditions are met, the fetal heart rate segment to be analyzed is the deceleration data segment, wherein $A_0$, $T_0$, $\beta$ and $\alpha$ are the parameters set in advance.

The invention, with a dynamic threshold area algorithm, a continuous peak inspection algorithm and a composite deceleration inspection algorithm, may effectively eliminate the baseline variation part, accurately identify each deceleration and the type thereof, and avoid the following disadvantages: the deceleration identification in the prior art is easily caused to have large errors; continuous deceleration may not be identified; baseline variation may not be eliminated; and composite deceleration may not be identified. The proposal is adapted for not only deceleration separately occurring (typical deceleration situation) but also for continuous deceleration and composite deceleration situations.

BRIEF DESCRIPTION OF THE DRAWINGS

For easy description, the invention is described with the following preferred examples and drawings.

DETAILED DESCRIPTION OF THE EMBODIMENTS

In order that the objective, technical proposal and advantages of the invention are better described, the invention is further described in details with the combination of drawings and embodiments in the following: It shall be understood that the embodiments described herein are merely used for explaining the invention and not used for limiting the invention.

Figure 1:
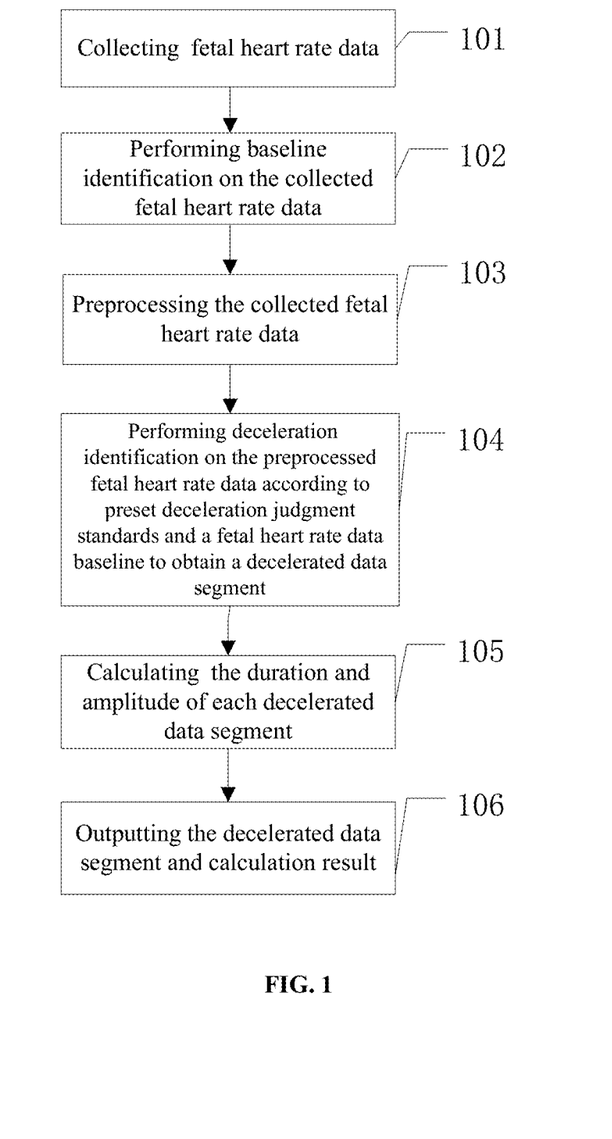
FIG. 1 is an example flow chart of a method for improving the identification accuracy of a fetal heart rate data according to the invention.

The technical proposal for automatically identifying the fetal heart rate deceleration is realized mainly through an upper computer and a lower computer, wherein the lower computer collects a fetal heart rate signal mainly through an ultrasound probe and then calculates the fetal heart rate through a hardware filtered process and autocorrelation algorithm. The upper computer is mainly used for receiving the data from the lower computer and then displaying and storing the fetal heart rate data, depicting the fetal heart rate curve, as well as analyzing, displaying and printing the fetal heart rate data (comprising the identification of the fetal heart rate), wherein the main processing method is shown in FIG. 1:

101. Collecting the fetal heart rate data:

The upper computer collects n-minute fetal heart rate data and obtains the fetal heart rate data sequence H(n), wherein in the example, at least ten minutes of data shall be needed to be collected. According to "Fetal Electronic Monitor", generally, at least ten minutes of data are needed to determine the fetal heart rate baseline.

Figure 5:
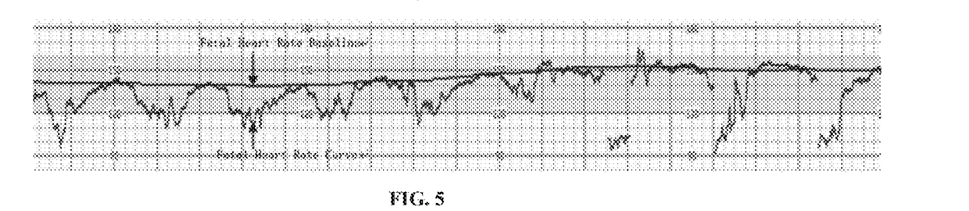
FIG. 5 is a schematic diagram of collected fetal heart rate data and an identified fetal heart rate baseline.

102. Identifying the baseline of the collected fetal heart rate data:

According to the sequence H(n), the fetal heart rate baseline data sequence B(n) is identified with the adoption of a low-pass filtered method. Comparing to the fetal heart rate data, the baseline belongs to the low frequency signal. A low-pass filter is characterized in that low-frequency signals may be passed through the filter while high-frequency signals may not be passed through the filter, thus extracting the low frequency signals of the fetal heart rate baseline. In addition, in this step, the data in the sequence H(n) may also be firstly processed. After the data are processed with an incorrect data processing method, an average filtering method and a linear interpolation method, the fetal heart rate baseline is identified according to the data. FIG. 5 shows collected fetal heart rate data and an identified fetal heart rate baseline;

103. Preprocessing the collected fetal heart rate data:

The sequence H(n) is processed with the incorrect data processing method and the linear interpolation method in sequence and then obtains the fetal heart rate data sequence corresponding to different preprocessing processes.

104. Performing deceleration identification on the preprocessed fetal heart rate data according to the deceleration judgment standard and the fetal heart rate baseline to obtain the deceleration data segment.

The sequence segment, meeting the conditions, is judged according to the preprocessed judgment standard. And according to the sequence segment and the corresponding baseline sequence segment thereof, deceleration and baseline variation sequence segments in the sequence segment are inspected and distinguished, and the number of continuous decelerations of the deceleration sequence segment is analyzed.

105. Calculating the deceleration attribute values of each deceleration data segment:

According to the original point, destination point and duration of each deceleration, the maximum amplitude value deviating from the baseline in the deceleration is calculated.

106. Outputting the deceleration data segment and the calculation results:

The example preferably displays and/or prints and/or stores the identified deceleration data segment and the calculated results.

Figure 2:
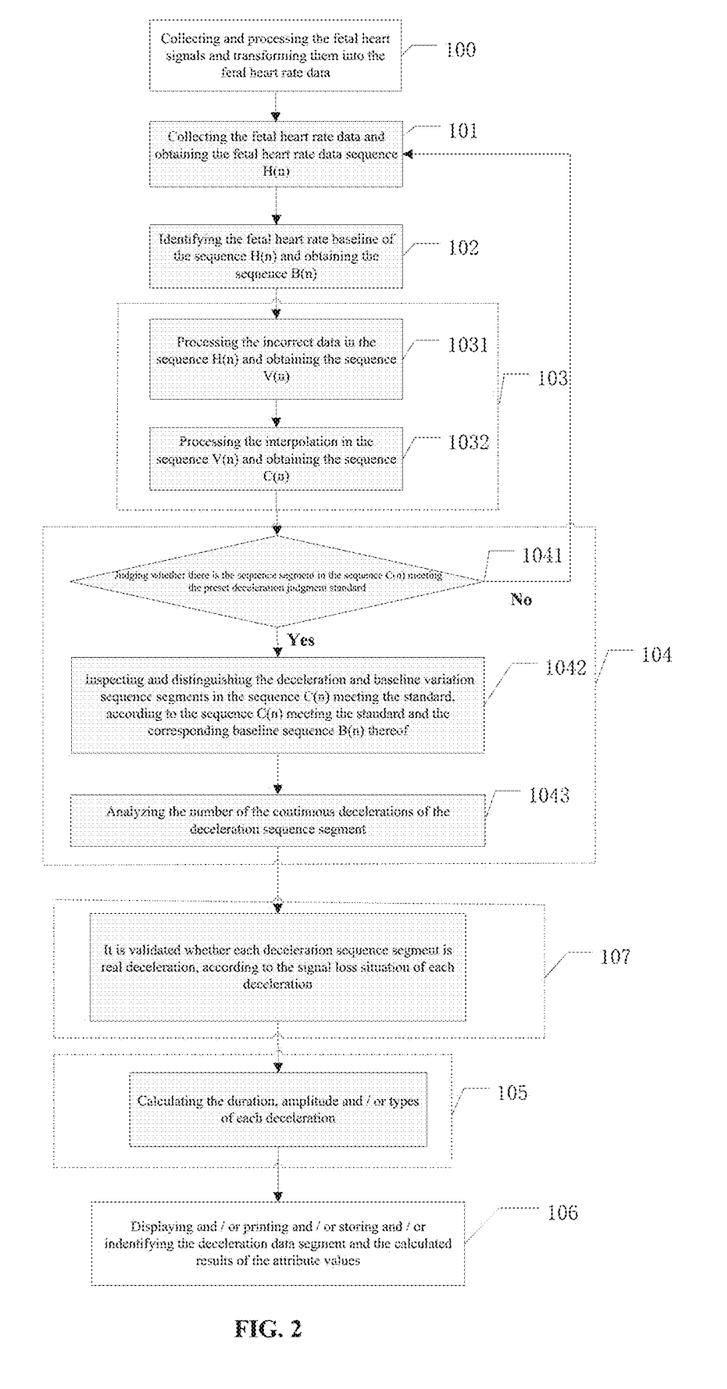
FIG. 2 is an another example flow chart of a method for improving the identification accuracy of a fetal heart rate data according to the invention.

In order to better understand the invention, as another example of the invention, FIG. 2 shows the flow chart of a method for improving the identification accuracy of the fetal heart rate data deceleration in the following:

100. Collecting and processing the fetal heart signals and transforming them into the fetal heart rate data:

After the fetal heart signal received by an ultrasound probe in the lower computer is filtered by hardware and calculates the fetal heart rate according to the autocorrelation algorithm, it is uploaded to the upper computer. The processing of the upper computer comprises: displaying, storing and depicting the fetal heart rate data into a fetal heart rate curve and processing the related data, etc. wherein, the hardware filtering is used for removing the frequency interference of the collected signals, and the autocorrelation algorithm is characterized in that it may strengthen a periodic signal and weaken stochastic noise, which are the general techniques for calculating the fetal heart rate data.

101. Collecting the fetal heart rate data and obtaining the fetal heart rate data sequence H(n):

The upper computer collects n-minute fetal heart rate data and obtains the fetal heart rate data sequence H(n), wherein in the example, at least ten minutes of data shall be needed to be collected. According to "Fetal Electronic Monitoring", generally, at least ten minutes of data are needed to determine the fetal heart rate baseline.

102. Identifying the fetal heart rate baseline in the sequence H(n) and obtaining the sequence B(n);

According to the sequence H(n), the fetal heart rate baseline B(n) is identified with the adoption of the low-pass filtered method. Comparing to the fetal heart rate data, the baseline belongs to the low frequency signal. A low-pass filter is characterized in that low-frequency signals may be passed through the filter while high-frequency signals may not be passed through the filter, thus extracting the low frequency signals of the fetal heart rate baseline. In addition, in this step, the data in the sequence H(n) may also be firstly processed. After the data are processed with an incorrect data processing method, an average filtering method and a linear interpolation method, the fetal heart rate baseline is identified according to the data. FIG. 5 shows collected fetal heart rate data and an identified fetal heart rate baseline. In addition, there are many methods for identifying the fetal heart rate data baseline, for example, an averaging method generally adopted in the industry, etc.

1031. Processing the incorrect data in the sequence H(n) and obtaining the sequence V(n):

The incorrect data in the sequence H(n) are processed to obtain the effective fetal heart rate data sequence V(n). This step may effectively filter out the invalid and incorrect data in the fetal heart sequence generated because of poor quality of the fetal heart signals, and the rest are valid data.

Figure 6:
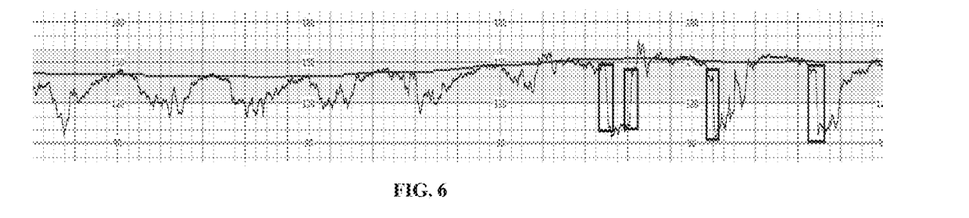
FIG. 6 is an effect diagram of a preprocessed fetal heart rate data sequence.

1032. Processing the sequence V(n) with interpolation and obtaining the sequence C(n):

The invalid data in the sequence V(n) are fitted with the linear interpolation method obtaining the sequence C(n). The linear interpolation method is a simple interpolation method in which other points in a straight line are obtained with a principle of forming a straight line by connecting two points. FIG. 6 is an effect diagram of a preprocessed fetal heart rate data sequence. The fetal heart rate curve part in a square frame in the Figure is just the curve section obtained after the incorrect data are processed with the interpolation.

In Steps 1031 and 1032, the collected fetal heart rate data are preprocessed. In addition, the fetal heart rate data preprocessing step is not limited to the above steps. It can also adopt the following methods informed in the industry: the fetal heart rate value with bpm (beats per min) as the unit is divided with incorrect data and/or moving average and/or interpolation fitting, etc.

1041. It is judged whether there is a sequence segment in the sequence C(n) meeting the preset deceleration judgment standard:

The deceleration judgment standards which are preferably preset in the example are as follows:

As to one section of the fetal heart rate curve, it may be determined to be in deceleration only when it meets all of the following conditions:

Firstly, the section of the fetal heart rate curve of the segment shall all be under the fetal heart rate baseline;

Secondly, the duration T under the fetal heart rate baseline shall be more than or equal to the threshold $T_0$; and Thirdly, the maximum amplitude A deviating from the baseline shall be more than or equal to the threshold $A_0$.

Fourthly, the area S is obtained from the fetal heart rate curve according to complexification value integration principle. Its process is as follows: the fetal heart rate curve of the segment and the corresponding baseline segment thereof are set as $$\{C_i\}_{S_i}^{E_i}$$

and $$\{B_i\}_{S_i}^{E_i},$$

respectively;

$$\{B_i\}_{S_i}^{E_i}$$

and $$\{C_i\}_{S_i}^{E_i}$$

are differenced to obtain the sequence segment $$\{D_i\}_{S_i}^{E_i}; \{D_i\}_{S_i}^{E_i}$$

is calculated with the compound trapezoid formula with step h to obtain the area S, wherein S shall be greater than or equal to the minimum value of the dynamic threshold β and the static threshold α×A×T;

The judgment condition improves the judgment standard, thus facilitating the judgment to be more accurate, wherein the parameters $A_0$, $T_0$, β and α are the preset experiential parameters and set differently with the different input of the gestational week parameters.

The sequences C(n) and B(n) are input into the deceleration judgment standard, thus obtaining the set $$\{\{C_i\}_{S_i}^{E_i}\}_1^N$$

of each sequence segment meeting the deceleration standard in the sequence C(n) and the corresponding baseline sequence segment set $$\{\{B_i\}_{S_i}^{E_i}\}_1^N$$

thereof. If there is no sequence segment meeting the deceleration standard, it means that there is not deceleration in the fetal heart rate curve. At this time, the identification of the fetal heart rate deceleration may be ended, and the fetal heart rate data are collected once again.

1042. According to the sequence C(n) meeting the standard and the corresponding baseline sequence B(n) thereof, deceleration and baseline variation sequence segments in the sequence C(n) meeting the standard are inspected and distinguished.

As to each sequence segment $$\{C_i\}_{S_i}^{E_i}, \{C_i\}_{S_i}^{E_i} \text{ and } \{B_i\}_{S_i}^{E_i}$$

are differenced to obtain the sequence segment $$\{D_i\}_{S_i}^{E_i}.$$

The continuous sequence segment, which is not more than threshold $R_0$, is sought in the sequence segment $$\{D_i\}_{S_i}^{E_i}.$$

If there is no sequence segment in the sequence $$\{D_i\}_{S_i}^{E_i}$$

meeting the condition, the sequence segment $$\{C_i\}_{S_i}^{E_i}$$

consists of one deceleration group or continuous deceleration groups. The number of decelerations is analyzed with the continuous peak inspection algorithm method in the next step. If there is a sequence segment meeting the condition in $$\{C_i\}_{S_i}^{E_i},$$

the sequence segment at the corresponding place and in the $$\{C_i\}_{S_i}^{E_i}$$

is judged as the baseline variation part which is recorded as $$\{\{C'_j\}_{S'_j}^{E'_j}\}_1^M,$$

wherein $$\{C'_j\}_{S'_j}^{E'_j} \subseteq \{C_i\}_{S_i}^{E_i}.$$

At this time, the baseline variation part divides the $$\{C_i\}_{S_i}^{E_i}$$

into a plurality of segments which are recorded as $$\left\{\{\overline{C}'_k\}_{S'_k}^{E'_k}\right\}_1^{N_2},$$

wherein $$\{\overline{C}'_k\}_{S'_k}^{E'_k} \subseteq \{C_i\}_{S_i}^{E_i}.$$

It is judged whether $$\{\overline{C}'_k\}_{S'_k}^{E'_k}$$

meets the deceleration standard. If it meets the deceleration standard, $$\{\overline{C}'_k\}_{S'_k}^{E'_k}$$

is one deceleration group or continuous deceleration groups, and the number of the decelerations is analyzed with the continuous peak inspection algorithm in the next step. If it does not meet the deceleration standard, $$\{\overline{C}'_k\}_{S'_k}^{E'_k}$$

is the baseline variation part. With this step, the deceleration part and the baseline variation part may be distinguished.

1043. Analyzing the number of continuous decelerations of the deceleration sequence segment:

As to each fetal heart rate sequence segment (here, it may be $$\{C_i\}_{S_i}^{E_i} \text{ or } \{\overline{C}'_k\}_{S'_k}^{E'_k})$$

to be analyzed, there is $$\{\overline{C}'_k\}_{S'_k}^{E'_k} \subseteq \{C_i\}_{S_i}^{E_i}.$$

The process analyzed with the continuous peak inspection algorithm is as follows: the continuous sequence segment, of which the deviation value of the corresponding baseline is not more than the threshold R1, is sought in the segment. If there is no sequence segment (all deviation values exceed the threshold R1) meeting such condition, the $$\{\overline{C}'_k\}_{S'_k}^{E'_k}$$

is one deceleration. If there is a sequence segment meeting such condition, recording as the $$\left\{\{\overline{C}''_k\}_{S''_k}^{E''_k}\right\}_1^{M_2},$$

wherein $$\{\overline{C}''_k\}_{S''_k}^{E''_k} \subseteq \{\overline{C}'_k\}_{S'_k}^{E'_k}.$$

And it is then analyzed whether each segment $$\{\overline{C}''_k\}_{S''_k}^{E''_k}$$

separately meets the deceleration standard. If the segment $$\{\overline{C}''_k\}_{S''_k}^{E''_k}$$

may meet the deceleration standard, $$\{\overline{C}''_k\}_{S''_k}^{E''_k}$$

separately becomes the deceleration; otherwise, $$\{\overline{C}''_k\}_{S''_k}^{E''_k}$$

is incorporated into the segment $$\{\overline{C}''_k\}_{S''_k}^{E''_k},$$

Figure 7:
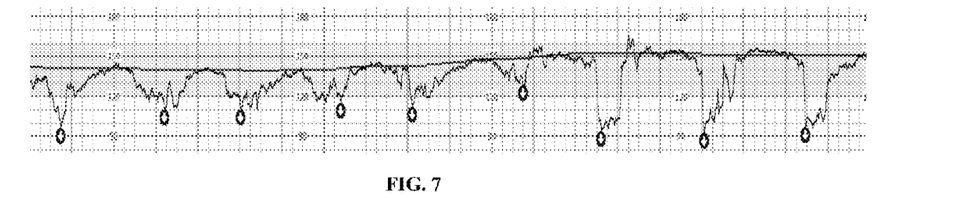
FIG. 7 is an effect diagram of the deceleration identification of a fetal heart rate data sequence.

Its adjacent segments are facilitated to be continuous and analyzed whether they meet the deceleration standard. If the deceleration standard is met, the continuous data segment becomes one deceleration, and the subsequent segment data are analyzed according to the deceleration standard continuously again. Otherwise, the baseline incorporates the segment until all of the segments are incorporated. With this step, continuous deceleration is identified. FIG. 7 is an effective diagram of deceleration identification. The fetal heart rate curve part in the square frame in the figure is the baseline variation part. The curve segment part designated with the Arrow ▬ is the identified fetal heart rate deceleration curve segment.

The abovementioned Steps 1041, 1042 and 1043 are used for performing deceleration identification of the processed and collected fetal heart rate data. So far, this step has completed the identification for the deceleration data segment of the invention. Steps 105 and 106 may be directly entered into to calculate the attribute values and output the results, or Step 106 is directly entered into to output the calculated results. In order to facilitate the results to be more accurate, the example also may preferably adopt the following deceleration validation steps prior to the steps of calculation and result output.

Figure 8:
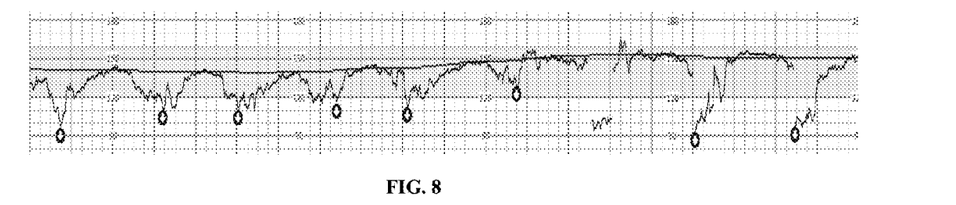
FIG. 8 is an effect diagram of the deceleration validation of a fetal heart rate data sequence.

107. It is validated whether each deceleration sequence segment is real deceleration, according to the signal loss situation of each deceleration:

If the deceleration of the above steps is obtained according to the interpolated sequence, it means that the deceleration is obtained without consideration of the situation of signal loss. In this step, the deceleration shall be validated and the signal loss in each pre-deceleration shall be analyzed, thus determining whether each pre-deceleration is retained and split, and finally obtaining the real deceleration. The step also comprises the following processed processes:

The first step: comparing the sequences V(n) and C(n) and marking the interpolation place to obtain a marked sequence M(n);

The second step: as to each deceleration, adjusting the places of original and destination points according to the sequence M(n) and facilitating the original and destination points not to be the interpolation points and to be closest to the interpolation point; and The third step: the adjusted signal loss degree L is calculated. The signal loss degree is the number (being equal to the number of the interpolation points) of the invalidated values in the fetal heart rate deceleration curve data and the proportion of the invalidated values against the whole part. If the L exceeds the threshold $\overline{L}$, the qualification of the deceleration shall be cancelled. Otherwise, the qualification of the deceleration is retained. FIG. 8 is an effective diagram of deceleration validation.

The arrow icon in the figure indicates the deceleration.

Figure 9:
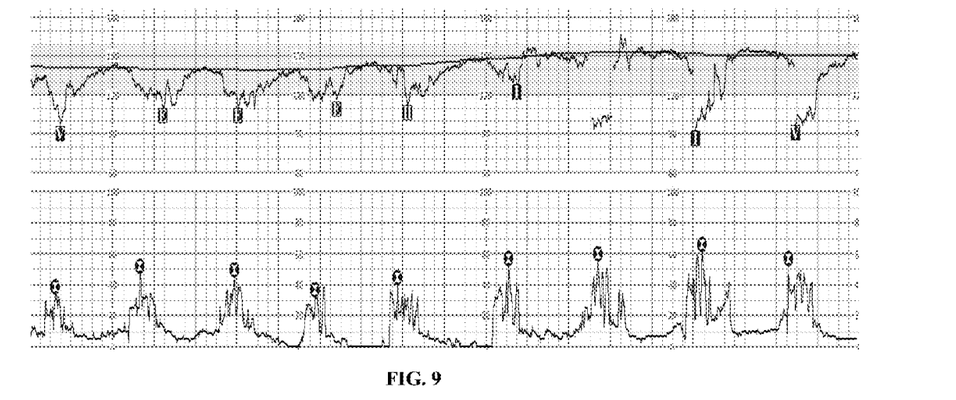
FIG. 9 is an effect diagram of the identification of the deceleration type of a fetal heart rate data sequence when there are uterine contraction data.

105. Calculating the duration, amplitude and/or type of each deceleration:

Calculating the duration $D_S$ according to the original point $D_E$ and the destination point $D_T$ of each deceleration, calculating the maximum amplitude $D_A$ deviating the baseline in the deceleration and recording the place $D_P$ of the point (peak point);

In addition, if the type of the deceleration may be judged while the uterine contraction data are collected, then if the uterine contraction data are not collected, the final deceleration displaying effective diagram is in line with FIG. 8. If the uterine contraction data are collected, the process that the type of deceleration is determined with the adoption of composite deceleration inspection algorithm is as follows: Judgment conditions 1: $D_S$ is subtracted by $D_P$ and obtains $D_{PS}$ which is greater than or equal to the threshold $T_E^1$; the absolute value obtained from the uterine contraction original point $U_S$ subtracted by $D_S$ is less than or equal to the threshold $T_E^2$; and the absolute value obtained from the uterine contraction peak place $U_P$ subtracted by $D_P$ is less than or equal to the threshold $T_E^3$. Judgment conditions 2: $D_S$ is subtracted by $D_P$ and obtains $D_{PS}$ which is greater than or equal to the threshold $T_L^1$; $D_{ES}$ obtained from the $D_S$ subtracted by $D_E$ is greater than or equal to the threshold $T_L^2$; the value obtained from the uterine contraction peak place $U_P$ subtracted by $D_P$ is greater than or equal to the threshold $T_L^3$ and is less than or equal to the threshold $T_L^4$; and $D_E$ is greater than the uterine contraction destination point $U_E$. Judgment conditions 3: $D_{PS}$ obtained from the $D_S$ subtracted by $D_P$ is less than the threshold $T_V^1$; $D_T$ is greater than or equal to the threshold $T_V^2$ and is less than the threshold $T_V^3$; and $D_A$ is greater than or equal to the threshold $A_V^1$. Judgment conditions 4: $D_T$ is greater than or equal to the threshold $T_P^1$ and less than the threshold $T_P^2$; and $D_A$ is greater than or equal to the threshold $A_P^1$. If the judged deceleration data meet judgment conditions 1, the deceleration data are judged to be early deceleration. If they meet judgment conditions 2, they are judged as late deceleration. If they meet judgment conditions 3, they are judged as variable deceleration. If they meet judgment conditions 4, they are judged as prolonged deceleration. Each deceleration datum is input into the four judgment conditions. If only one judgment condition is met, the deceleration is judged to be a typical deceleration, that is, a single-type deceleration. If many judgment conditions are met, the deceleration is judged to be an atypical deceleration, that is, a composite-type deceleration. Meanwhile, the deceleration is determined to be what type of composite deceleration according to the conditions met by the deceleration. FIG. 9 is an effective diagram of the identification of deceleration type when there are uterine contraction data. In the figure, ◨ indicates early deceleration; ◩ indicates variable deceleration; ◫ indicates a composite of early deceleration and variable deceleration; and ◨ indicates a composite of late deceleration and variable deceleration.

106. Displaying and/or printing and/or storing and/or identifying the deceleration data segment and the attribute values:

The identified deceleration data segments are respectively input into a displaying module, a printing module and a storage module. Each deceleration data segment and the attribute values thereof are also identified and displayed in the fetal monitoring drawing. Its attribute values may be stored and printed.

Figure 3:
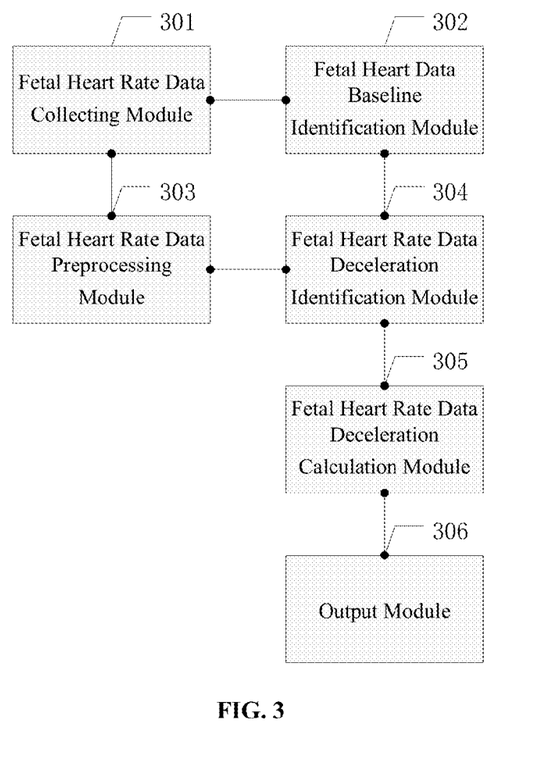
FIG. 3 is an example site structure of a device for improving the identification accuracy of a fetal heart rate data according to the invention.

In order to better explain the invention, an example site structure of a device for improving the identification accuracy of a fetal heart rate data is provided, which is shown in FIG. 3:

A fetal heart rate data collection module 301:

The module 301 is used for collecting the fetal heart rate data with preset duration and obtaining the fetal heart rate data sequence H(n);

A fetal heart rate data baseline identification module 302:

The module 302 is connected with the fetal heart rate data collection module 301 and used for receiving the fetal heart rate data sequence H(n) transmitted by the fetal heart rate data collection module 301 and identifying the fetal heart rate baseline sequence B(n);

A fetal heart rate data preprocessing module 303:

The module 303 is connected with the fetal heart rate data collection module 301 and used for receiving the fetal heart rate data sequence H(n) transmitted by the fetal heart rate data collection module 301, and preprocessing the sequence H(n) to obtain the fetal heart rate data sequence V(n);

A fetal heart rate data deceleration identification module 304:

The module 304 is connected with the fetal heart rate data baseline identification module 302 and the fetal heart rate data preprocessing module 303 and used for receiving the fetal heart rate data baseline sequence B(n) transmitted by the fetal heart rate data baseline identification module 302 and the preprocessed sequence V(n) transmitted by the fetal heart rate data preprocessing module 303. The deceleration identification for the preprocessed fetal heart rate data sequence V(n) is performed to obtain a decelerated data segment, according to the preset deceleration judgment standards and the fetal heart rate data baseline sequence B(n).

A fetal heart rate data deceleration attribute calculation module 305:

The module 305 is connected with the fetal heart rate data deceleration identification module 304 and used for receiving the deceleration data segment transmitted by the fetal heart rate data deceleration identification module 304 and calculating the duration, amplitude and other deceleration attributes of each the deceleration data segment.

An output module 306:

The output module 306 is connected with the fetal heart rate data deceleration attribute calculation module 305 and used for receiving the deceleration data segment and the deceleration attribute calculation results thereof transmitted by the fetal heart rate data deceleration attribute calculation module 305, and outputting them.

Figure 4:
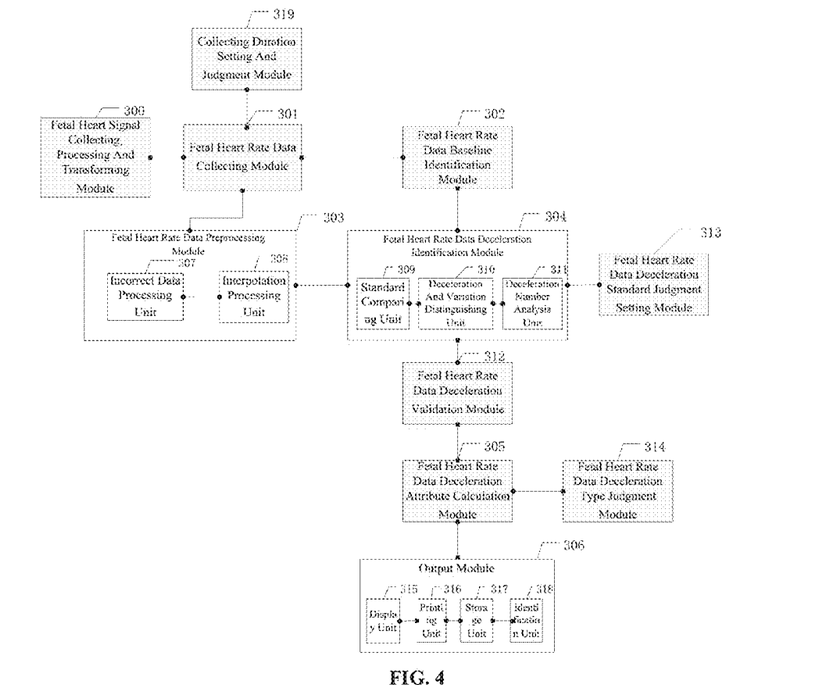
FIG. 4 is an another example site structure of a device for improving the identification accuracy of a fetal heart rate data according to the invention.

In order to better explain the invention, another example site structure of a device for improving the identification accuracy of a fetal heart rate data is provided, which is shown in FIG. 4:

A device for improving identification accuracy of fetal heart rate deceleration also comprises:

A fetal heart signal collection, processing and transformation module 300:

The module 300 is connected with the fetal heart rate data collection module 301, is an ultrasound probe device realizing the collection, process and transformation of the signals, as well as is used for collecting the fetal heart signals, transforming them into the fetal heart rate data and transmitting the fetal heart rate data to the fetal heart rate data collection module 301.

A fetal heart rate data deceleration validation module 312:

The module 312 is connected with the fetal heart rate data deceleration identification module 304 and the fetal heart rate data deceleration attribute calculation module 305 and is used for receiving the deceleration data segment transmitted by the fetal heart rate data deceleration identification module 304, validating whether each deceleration sequence segment is real deceleration according to the signal loss situation of each deceleration, and transmitting the validated results to the fetal heart rate data deceleration attribute calculation module 305.

A fetal heart rate data deceleration standard judgment setting module 313:

The module 313 is connected with the fetal heart rate data deceleration identification module 304 and used for setting the fetal heart rate data deceleration judgment standard in advance and transmitting the standard to the fetal heart rate data deceleration module 304.

A fetal heart rate data deceleration type judgment module 314:

The module 314 is connected with the fetal heart rate data deceleration attribute calculation module 305 and used for judging the deceleration type under the conditions of collecting the uterine contraction data, and transmitting the judged results to the fetal heart rate data deceleration attribute calculation module 305.

A collection duration setting and judgment module 319:

The module 319 is connected with the fetal heart rate data collection module 301 and used for setting the collection duration of the fetal heart rate data, and judging whether the collection data time exceeds the set duration. If it exceeds the set duration, a timeout signal is transmitted to the fetal heart rate data collection module 301.

In addition, the fetal heart rate data preprocessing module 303 further comprises:

an incorrect data processing unit 307 used for processing the incorrect data of the fetal heart rate data sequence H(n) and obtaining the effective fetal heart rate data sequence V(n);

an interpolation processing unit 308 used for fitting an invalid data part in the effective fetal heart rate data sequence V(n) with a linear interpolation method to obtain the fetal heart rate data sequence C(n).

the fetal heart rate data deceleration identification module 304 further comprises:

a standard comparison unit 309 used for judging whether there is a sequence segment meeting a preset deceleration judgment standard in the fetal heart rate data sequence C(n);

a deceleration and variation distinguishing unit 310 used for inspecting and distinguishing deceleration and baseline variation sequence segments in the sequence C(n) meeting the standard, according to the fetal heart rate data sequence C(n) meeting the judgment standard and the corresponding baseline sequence B(n) thereof; and a deceleration number analysis unit 311 used for analyzing the continuous deceleration number of a deceleration sequence in the sequence C(n) meeting the standard.

the output module 306 further comprises:

a display unit 315 used for displaying an identified deceleration data segment and an attribute value thereof;

a printing unit 316 used for printing and outputting the identified deceleration data segment and the attribute value thereof;

a storage unit 317 used for storing the identified deceleration data segment and the attribute value thereof; and an identification unit 318 used for identifying the identified deceleration data segment and the attribute value thereof.

The abovementioned examples are only the preferred examples of the invention and do not limit the invention. Any modification, equal replacement and improvement within the spirit and principle of the invention shall be included in the scope of protection of the invention.

The invention claimed is:

1. A device for improving identification accuracy of fetal heart rate deceleration, wherein the device comprises a fetal heart rate data collection module, a fetal heart rate data baseline identification module, a fetal heart rate data preprocessing module, a fetal heart rate data deceleration identification module and an output module;

the fetal heart rate data collection module is used for collecting fetal heart data of a preset duration to obtain a fetal heart rate data sequence H(n);

the fetal heart rate data baseline identification module is connected with the fetal heart rate data collection module to be used for receiving the fetal heart rate data sequence H(n) transmitted by the fetal heart rate data collection module and identifying a fetal heart rate baseline sequence B(n);

the fetal heart rate data preprocessing module is connected with the fetal heart rate data collection module to be used for receiving the fetal heart rate data sequence H(n) transmitted by the fetal heart rate data collection module and preprocessing the sequence H(n) to obtain a fetal heart rate data sequence V(n);

the fetal heart rate data deceleration identification module is connected with the fetal heart rate data baseline identification module and the fetal heart rate data preprocessing module to be used for receiving the fetal heart rate baseline sequence B(n) transmitted by the fetal heart rate data baseline identification module and the preprocessed sequence V(n) transmitted by the fetal heart rate data preprocessing module; and performing deceleration identification for the preprocessed fetal heart rate data sequence V(n) to obtain a decelerated data segment, according to preset deceleration judgment standards and the fetal heart rate data baseline sequence B(n), and the output module is connected with the fetal heart rate data deceleration identification module to be used for receiving and outputting the decelerated data segment transmitted by the fetal heart rate data deceleration identification module.

2. The device for improving identification accuracy of the fetal heart rate data deceleration according to claim 1, wherein the device for improving identification accuracy of the fetal heart rate deceleration also comprises a fetal heart rate signal collection and processing transformation module, a fetal heart rate data deceleration validation module, a fetal heart rate data deceleration judgment standard setting module, a fetal heart rate data deceleration type judgment module, a collection duration setting and judgment module and a fetal heart rate data deceleration attribute calculation module, wherein the fetal heart rate signal collection and processing transformation module is connected with the fetal heart rate data collection module to be used for collecting a fetal heart signal, transforming the signal into fetal heart rate data and transmitting the fetal heart rate data to the fetal heart rate data collection module;

the fetal heart rate deceleration validation module is connected with the fetal heart rate data deceleration identification module and the fetal heart rate data deceleration attribute calculation module to be used for receiving the decelerated data segment transmitted by the fetal heart rate data deceleration identification module; according to the loss condition of each decelerated signal, the fetal heart rate data deceleration validation module validates whether each decelerated sequence segment is real deceleration, and transmits the validation result to the fetal heart rate data deceleration attribute calculation module;

the fetal heart rate data judgment standard setting module is connected with the fetal heart rate deceleration identification module to be used for setting the fetal heart rate data deceleration judgment standards in advance and transmitting the judgment standards to the fetal heart rate data deceleration identification module;

the fetal heart rate data deceleration type judgment module is connected with the fetal heart rate data deceleration attribute calculation module to be used for judging the deceleration type under the conditions of collecting uterine contraction data and transmitting the judgment result to the fetal heart rate data deceleration attribute calculation module;

the collection duration setting and judgment module is connected with the fetal heart rate data collection module to be used for setting the fetal heart rate collection duration and judging whether the collection data time exceeds the set duration; If the collection data time exceeds the set duration, the collection duration setting and judgment module transmits a timeout signal to the fetal heart rate data collection module; and the fetal heart rate data deceleration attribute calculation module is connected with the fetal heart rate data deceleration identification module and the output module to be used for receiving the deceleration data segment transmitted by the fetal heart rate data deceleration identification module, calculating the duration, amplitude and other deceleration attribute values of the each deceleration data segment and transmitting the calculated values to the output module.

3. The device for improving the identification accuracy of the fetal heart rate data deceleration according to claim 1, wherein the fetal heart rate data preprocessing module further comprises:

an incorrect data processing unit used for processing the incorrect data of the fetal heart rate data sequence H(n) and obtaining the effective fetal heart rate data sequence V(n); and an interpolation processing unit used for fitting an invalid data part in the effective fetal heart rate data sequence V(n) with a linear interpolation method to obtain the fetal heart rate data sequence C(n).

4. The device for improving the identification accuracy of the fetal heart rate data deceleration according to claim 1, wherein the fetal heart rate data deceleration identification module further comprises:

a standard comparison unit used for judging whether there is a sequence segment meeting a preset deceleration judgment standard in the fetal heart rate data sequence C(n);

a deceleration and variation distinguishing unit used for inspecting and distinguishing deceleration and baseline variation sequence segments in the sequence C(n) meeting the standard, according to the fetal heart data sequence C(n) meeting the judgment standard and the corresponding baseline sequence B(n) thereof; and a deceleration number analysis unit used for analyzing the continuous deceleration number of a deceleration sequence in the sequence C(n) meeting the standard.

5. The device for improving the identification accuracy of the fetal heart rate data deceleration according to claim 1, wherein the output module further comprises:

a display unit used for displaying the identified deceleration data segment and the attribute value thereof;

a printing unit used for printing and outputting the identified deceleration data segment and the attribute value thereof;

a storage unit used for storing the identified deceleration data segment and the attribute value thereof; and an identification unit used for identifying the identified deceleration data segment and the attribute value thereof.

6. A method for improving the identification accuracy of a fetal heart rate data deceleration, wherein, the method comprises:

Step 1, collecting the fetal heart rate data within a preset duration to obtain a fetal heart rate data sequence H(n);

Step 2, performing baseline identification on the fetal heart rate data sequence H(n) to obtain a fetal heart rate baseline data sequence B(n);

Step 3, preprocessing the fetal heart rate data sequence H(n) to obtain a preprocessed fetal heart rate data sequence C(n);

Step 4, performing deceleration identification on the preprocessed fetal heart rate sequence C(n) to obtain a decelerated data segment, according to a preset deceleration judgment standard and the fetal heart rate data baseline sequence B(n); and Step 5, outputting each decelerated data segment and calculation results of the deceleration attribute value thereof.

7. The method for improving the identification accuracy of the fetal heart rate data deceleration according to claim 6, wherein before Step 1, the method further comprises: collecting and processing a fetal heart signal, transforming it and obtaining a fetal heart rate data.

8. The method for improving the identification accuracy of the fetal heart rate data deceleration according to claim 6, wherein Step 3 further comprises Step 31, processing the incorrect data of the fetal heart rate data sequence H(n) to obtain a sequence V(n); and Step 32, processing the interpolation of the sequence V(n) to obtain the preprocessed fetal heart rate data sequence C(n).

9. The method for improving the identification accuracy of the fetal heart rate data deceleration according to claim 6, wherein Step 4 further comprises Step 41, the sequences C(n) and B(n) are input into the preset deceleration judgment standard, thus obtaining the set $$\{\{C_i\}_{S_i}^{E_i}\}_1^N$$

of each sequence segment meeting the deceleration standard in the sequence C(n) and the corresponding baseline sequence segment set $$\{\{B_i\}_{S_i}^{E_i}\}_1^N$$

thereof; if there is no sequence segment meeting the deceleration judgment standard, the user shall go back to Step 1 and collect the fetal heart rate data again;

Step 42, $$\{C_i\}_{S_i}^{E_i} \text{ and } \{B_i\}_{S_i}^{E_i}$$

are differenced to obtain sequence segment $$\{D_i\}_{S_i}^{E_i};$$

the continuous sequence segment, which is not more than threshold $R_0$, is sought in the sequence segment $$\{D_i\}_{S_i}^{E_i};$$

if there is no sequence segment meeting the condition in $$\{D_i\}_{S_i}^{E_i},$$

the sequence segment $$\{C_i\}_{S_i}^{E_i}$$

is judged to be a deceleration sequence segment; if there is a sequence segment meeting the condition in $$\{C_i\}_{S_i}^{E_i},$$

the sequence segment at the corresponding place and in the $$\{C_i\}_{S_i}^{E_i},$$

meeting the condition, is judged as the baseline variation part which is recorded as $$\{\{C_j'\}_{S_j'}^{E_j'}\}_1^M;$$

the baseline variation part divides $$\{C_i\}_{S_i}^{E_i}$$

into a plurality of segments, wherein $$\{\{\overline{C}_k'\}_{S_k'}^{E_k'}\}_1^{N_2}$$

judges whether $$\{\overline{C}_k'\}_{S_k'}^{E_k'}$$

meets the deceleration standard. If it meets the deceleration standard, the $$\{\overline{C}_k'\}_{S_k'}^{E_k'}$$

is recorded as the deceleration sequence segment, otherwise, it is the baseline variation sequence segment, wherein $R_0$ is the parameter set in advance;

Step 43, the continuous sequence segment, which deviates from its corresponding baseline and of which the value exceeds threshold R1, is sought in the deceleration segment $$\{\overline{C}_k'\}_{S_k'}^{E_k'};$$

if there is no sequence segment meeting such condition, the $$\{\overline{C}_k'\}_{S_k'}^{E_k'}$$

is one deceleration; if there is a sequence segment meeting such condition, recording as the $$\{\{\overline{C}_k''\}_{S_k''}^{E_k''}\}_1^{M_2};$$

and it is then analyzed whether each segment $$\{\overline{C}_k''\}_{S_k''}^{E_k''}$$

separately meets the deceleration standard; if the segment $$\{\overline{C}_k''\}_{S_k''}^{E_k''}$$

may meet the deceleration standard, the $$\{\overline{C}_k''\}_{S_k''}^{E_k''}$$

separately becomes the deceleration; otherwise, the $$\{\overline{C}_k''\}_{S_k''}^{E_k''}$$

is incorporated into the segment $$\{\overline{C}_k''\}_{S_k''}^{E_k''}.$$

Its adjacent segments are facilitated to be continuous and analyzed whether they meet the deceleration standard; if the deceleration standard is met, the continuous data segment becomes one deceleration; the subsequent segment data are analyzed according to the deceleration standard continuously again; otherwise, the baseline incorporates the segment until all of the segments are incorporated, wherein R1 is a preset parameter.

10. The method for improving the identification accuracy of the fetal heart rate data deceleration according to claim 6, wherein after Step 4, the method also comprises: judging the signal loss situation of each deceleration data segment and validating whether each deceleration sequence segment is in real deceleration, according to the deceleration data segment.

11. The method for improving the identification accuracy of the fetal heart rate data deceleration according to claim 10, wherein the method comprises: judging the signal loss situation of each deceleration data segment according to the deceleration data segment; and the method of validating whether each deceleration sequence segment is in real deceleration further comprises:
   a. comparing the sequences V(n) and C(n) and marking the interpolation place to obtain a marked sequence M(n);
   b. as to each deceleration data segment, adjusting the places of original and destination points according to the sequence M(n) and facilitating the original and destination points not to be the interpolation points and to be closest to the interpolation point; and
   c. calculating the adjusted signal loss degree L; if the L exceeds threshold $\overline{L}$, the qualification of the deceleration is cancelled; otherwise, the qualification of the deceleration is retained, wherein $\overline{L}$ is a parameter set in advance.

12. The method for improving the identification accuracy of the fetal heart rate data deceleration according to claim 6, wherein before Step 5, the method further comprises: calculating the deceleration attribute value of each deceleration data segment.

13. The method for improving the identification accuracy of the fetal heart rate data deceleration according to claim 12, wherein calculating the deceleration attribute value of each deceleration data segment also comprises:

Step 51, calculating the duration $D_T$ according to the original point $D_S$ and the destination point $D_E$ of each deceleration, calculating the maximum amplitude $D_A$ deviating from the baseline in the deceleration and recording the place $D_P$ of the point (peak point);

Step 52, it is judged whether the uterine contraction data are collected at the same time; if the uterine contraction data are not collected, the type of the deceleration is not judged; if the uterine contraction data are collected, it is judged whether the deceleration data segment is early deceleration and/or late deceleration and/or variable deceleration and/or prolonged deceleration, according to the preset deceleration type judging conditions.

14. The method for improving the identification accuracy of the fetal heart rate data deceleration according to claim 6, wherein Step 6 further comprises: displaying and/or printing and/or storing and/or identifying the deceleration data segment and the calculation results of the attribute values.

15. The method for improving the identification accuracy of the fetal heart rate data deceleration according to claim 6, wherein the preset judgment standard in Step 4 further comprises:
   Firstly, the fetal heart rate curves of the segment shall all be under the fetal heart rate baseline;
   Secondly, the duration T under the fetal heart rate baseline shall be greater than or equal to the threshold $T_0$; and
   Thirdly, the maximum amplitude A deviating from the baseline shall be greater than or equal to the threshold $A_0$;
   Fourthly, the fetal heart rate curve of the segment and the corresponding baseline segment thereof are set as $$\{C_i\}_{S_i}^{E_i}$$

and $$\{B_i\}_{S_i}^{E_i},$$

respectively;

$$\{B_i\}_{S_i}^{E_i} \text{ and } \{C_i\}_{S_i}^{E_i}$$

are differenced to obtain the sequence segment $$\{D_i\}_{S_i}^{E_i}; \{D_i\}_{S_i}^{E_i}$$

is calculated with the compound trapezoid formula with step h to obtain the area S; and S shall be greater than or equal to the minimum value of the dynamic threshold $\alpha \times A \times T$ and the static threshold $\beta$;
   If all of the above conditions are met, the fetal heart rate segment to be analyzed is the deceleration data segment, wherein $A_0$, $T_0$, $\beta$ and $\alpha$ are the parameters set in advance.

* * * * *